United States Patent
Johnsen et al.

(10) Patent No.: US 10,117,736 B2
(45) Date of Patent: Nov. 6, 2018

(54) LOW RADIAL FORCE FILTER

(71) Applicant: Cook Medical Technologies LLC, Bloomington, IL (US)

(72) Inventors: Jeppe Dufresne Johnsen, Froerup (DK); Bent Oehlenschlaeger, Skensved (DK); Erik Rasmussen, Slagelse (DK); Palle Hansen, Bjaeverskov (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 459 days.

(21) Appl. No.: 14/819,087

(22) Filed: Aug. 5, 2015

(65) Prior Publication Data

US 2016/0038271 A1 Feb. 11, 2016

Related U.S. Application Data

(60) Provisional application No. 62/033,826, filed on Aug. 6, 2014.

(51) Int. Cl.
*A61F 2/01* (2006.01)

(52) U.S. Cl.
CPC .......... *A61F 2/01* (2013.01); *A61F 2002/011* (2013.01); *A61F 2002/016* (2013.01); *A61F 2220/0016* (2013.01); *A61F 2230/005* (2013.01); *A61F 2230/0054* (2013.01); *A61F 2230/0056* (2013.01); *A61F 2230/0093* (2013.01)

(58) Field of Classification Search
CPC .................................. A61F 2/01; A61F 2/013
See application file for complete search history.

(56) References Cited

U.S. PATENT DOCUMENTS

| | | |
|---|---|---|
| 5,669,933 A | 9/1997 | Simon et al. |
| 5,746,767 A | 5/1998 | Smith |
| 5,984,947 A | 11/1999 | Smith |
| 6,007,558 A | 12/1999 | Ravenscroft et al. |
| 6,273,901 B1 | 8/2001 | Whitcher et al. |
| 6,391,045 B1 | 5/2002 | Kim et al. |
| 6,482,222 B1 | 11/2002 | Bruckheimer et al. |
| 6,589,266 B2 | 7/2003 | Whitcher et al. |
| 7,056,286 B2 | 6/2006 | Ravenscrift et al. |
| 7,179,274 B2 | 2/2007 | Bruckheimer et al. |
| 7,211,107 B2 | 5/2007 | Bruckheimer et al. |
| 7,749,244 B2 | 7/2010 | Brucheimer et al. |

(Continued)

FOREIGN PATENT DOCUMENTS

EP    1 598 029 A2    10/1995

OTHER PUBLICATIONS

Cardinal Search Report dated Feb. 28, 2014.

*Primary Examiner* — Kathleen Holwerda
(74) *Attorney, Agent, or Firm* — Brinks Gilson & Lione

(57) ABSTRACT

The disclosure provides a filter apparatus and method of filtering in a body vessel. The filter apparatus comprises a filter unit and an expandable introducer designed to deliver the filter unit to the target filtering site. The filter unit attaches to the expandable introducer via a plurality of anchors on the filter unit. The expandable introducer delivers and presses the anchors to the vessel wall during implantation. After implantation, the filter unit exerts minimal or about zero radial force against the vessel wall.

20 Claims, 9 Drawing Sheets

(56) References Cited

U.S. PATENT DOCUMENTS

| | | |
|---|---|---|
| 7,976,562 B2 * | 7/2011 | Bressler .................. A61F 2/01 606/108 |
| 8,062,326 B2 | 11/2011 | McGuckin, Jr. et al. |
| 8,231,649 B2 | 7/2012 | Petersen |
| 8,273,099 B2 | 9/2012 | DiMatteo |
| 8,308,750 B2 | 11/2012 | Beulke |
| 8,317,818 B2 | 11/2012 | Kashkarov et al. |
| 8,398,672 B2 | 3/2013 | Kleshinski et al. |
| 8,409,239 B2 | 4/2013 | Kleshinski et al. |
| 8,500,774 B2 | 8/2013 | McGuckin, Jr. et al. |
| 8,647,360 B2 | 2/2014 | Gilson et al. |
| 2003/0199918 A1 | 10/2003 | Patel et al. |
| 2003/0208226 A1 | 11/2003 | Bruckheimer et al. |
| 2005/0101982 A1 * | 5/2005 | Ravenscroft ..... A61B 17/12022 606/182 |
| 2006/0015137 A1 | 1/2006 | WasDyke et al. |
| 2006/0036279 A1 | 2/2006 | Eidenschink et al. |
| 2006/0206138 A1 * | 9/2006 | Eidenschink ............ A61F 2/01 606/200 |
| 2008/0188887 A1 | 8/2008 | Batiste |
| 2008/0275492 A1 * | 11/2008 | Farmiga .................. A61F 2/01 606/200 |
| 2009/0005803 A1 | 1/2009 | Batiste |
| 2010/0076545 A1 | 3/2010 | Kleshinski et al. |
| 2010/0318115 A1 | 12/2010 | Chanduszko et al. |
| 2011/0257677 A1 | 10/2011 | Carr, Jr. et al. |
| 2012/0078286 A1 | 3/2012 | Salik |
| 2012/0221040 A1 | 8/2012 | Eggers |
| 2012/0245619 A1 * | 9/2012 | Guest .................... A61F 2/01 606/200 |
| 2013/0072962 A1 | 3/2013 | Beulke |
| 2013/0138137 A1 | 5/2013 | Molgaard-Nielsen |
| 2013/0218195 A1 | 8/2013 | Kleshinski et al. |
| 2013/0261638 A1 | 10/2013 | Diamant et al. |

* cited by examiner

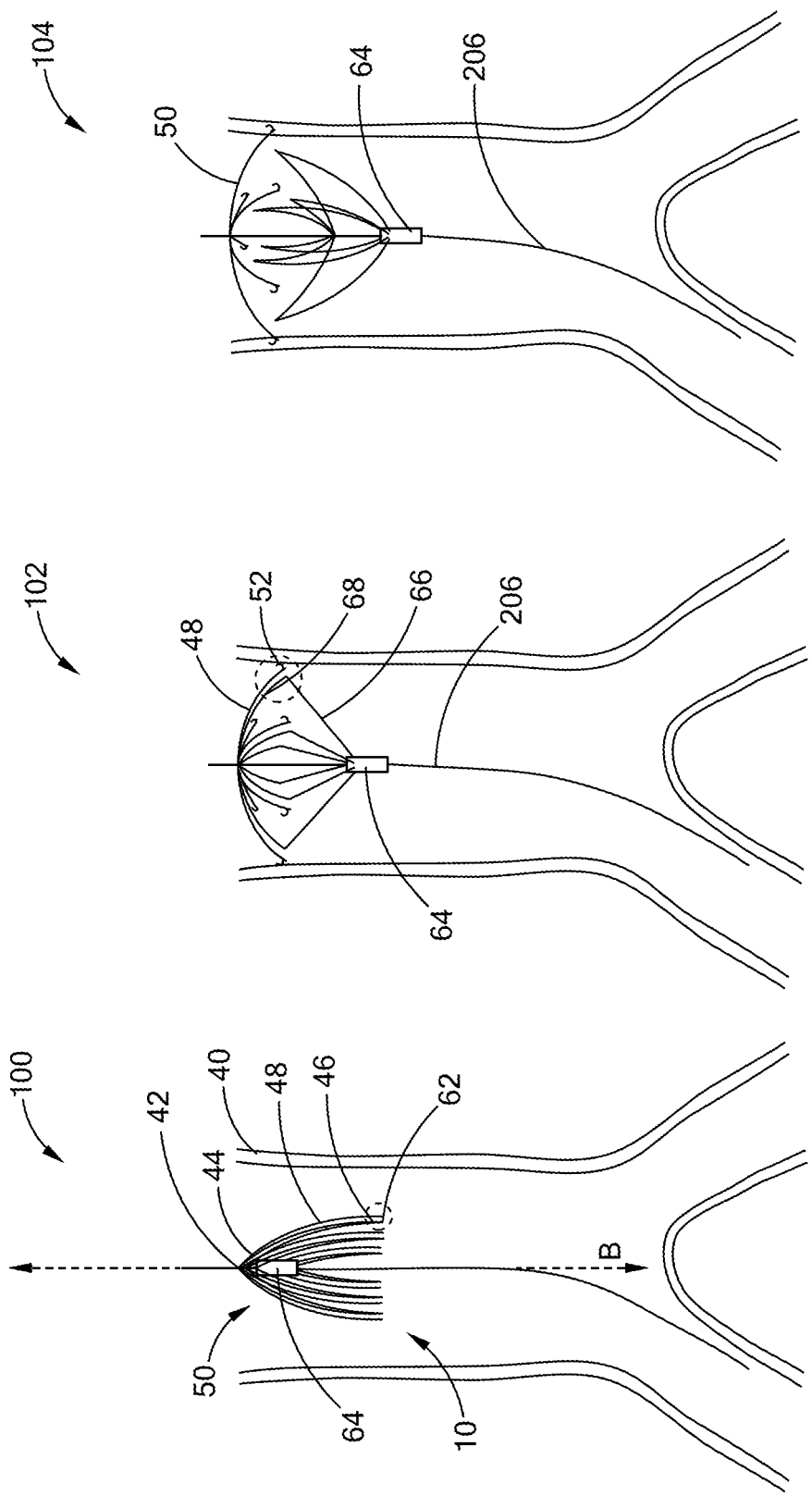

LOW RADIAL FORCE FILTER

CROSS-REFERENCE TO RELATED APPLICATIONS

This application claims priority under 35 U.S.C. § 119(a) to U.S. Provisional Patent Application Ser. No. 62/033,826, filed Aug. 6, 2014, entitled "LOW RADIAL FORCE FILTER," the entire contents of which are hereby incorporated by reference.

BACKGROUND

1. Technical Field Text

The present disclosure relates to medical devices. More particularly, the disclosure relates to a low radial force filter for filtering thrombi in a body vessel.

2. Background Information

The vena cava is the largest vein in the body. It returns deoxygenated blood to the heart. The anatomy of the vena cava is flexible, and the vena cava moves with the diaphragm as it expands and contracts during breathing. Vena cava filters are common prophylactic devices to prevent pulmonary embolisms caused by deep vein thrombosis. Such filters can be placed using minimally invasive techniques, either from the jugular or femoral vein.

Current filter devices typically may require enough stiffness that the filter exerts a force on the circumference of the body vessel in which it is placed (i.e. vena cava wall). This force against the wall, typically exerted through struts or other filter appendages, aids in maintaining the filter in place (i.e. anti-migration). However, the literature shows that over time this force may have unintended consequences, such as tenting of the vessel walls. Over the time the filter is implanted, tenting may become more pronounced. Further, because typical filters may require sufficient stiffness to push on the vessel wall, they may also have internal forces pushing on other parts of the filter. The literature suggests that over time such internal forces may fatigue.

In addition, typical filters may employ barbs to attach to the vessel wall. Such barbs may also have the same stiffness as other parts of the filter. These barbs may become endothelialized into the vessel wall. Depending on the barbs' geometry, they may be difficult to remove after endothelialization. It may also be difficult for the physician to tell if the barbs have penetrated through the wall. Based on these possible consequences, there is a need for an improved device.

BRIEF SUMMARY

The present disclosure provides for an example of a filter apparatus and method of filtering with no or minimal radial force which is also easily retrievable. The present disclosure provides generally for one example of a method of filtering in a body vessel (i.e. vena cava) for maintained vessel flexibility.

The disclosure provides an example of an implantation and removal method in a body vessel, the body vessel having a wall and a longitudinal axis. The body vessel may be being accessible from multiple locations (e.g. a femoral or a jugular access point). The method includes; first, positioning the filter apparatus in the body vessel. The filter apparatus includes the features discussed further herein. Second, the method includes contacting the anchor against the wall with the expandable introducer by moving the apparatus from the collapsed state to the expanded state; and third, attaching or fixing the anchor to the wall by removing the anchor from the casing.

The method further includes expanding the expandable introducer after the step of positioning, the expandable introducer having a slider connected to a plurality of introducer levers, each introducer lever extending to a one of a plurality of filter carriers, the step of expanding including moving the slider to extend the filter carriers and introducer levers toward the wall. The method further includes inverting the expandable introducer after the step of attaching. The method may also include withdrawing the expandable introducer after the step of inverting. Additionally, the method further includes retrieving the filter unit with a retriever after the step of inverting (e.g. femoral or jugular retrieval).

In one embodiment, the step of positioning comprises positioning the anchor made from a bio-absorbable material. The step of attaching includes the filter legs exerting about zero radial force on the wall. Additionally, the step of attaching includes the anchor curling from a straight state in the casing to a curled state attached or fixed to the wall. The step of retrieving includes the anchor uncurling from a curled state fixed to the wall to a straight state for retrieval of the filter unit.

The filter apparatus itself may include a filter unit and an expandable introducer. The filter unit has a filter point (e.g. a center) and a plurality of filter legs extending from the filter point. Each filter leg includes a first end and a second end, the first end extending outward from the filter point to the second end, the second end including an anchor being biased to curl. The expandable introducer has a casing removably attached to the filter unit at the anchor. The apparatus may have a collapsed state and an expanded state for attaching the filter unit to the wall. In one embodiment, the plurality of filter legs is eight to sixteen filter legs. In this embodiment, each filter leg has a curve. In another embodiment, the plurality of filter legs is formed into an interwoven net or mesh.

The anchor may have a straight state for delivery and a curled state for attaching to the wall. The anchor may have an open loop extending from the second end to a sharp point in the curled state, the open loop extending in a curl from the second end to a sharp point. The anchor may have three embodiments. First, the sharp point may be disposed to face one filter leg adjacent to the second end. In this condition, each filter leg and its respective open loop may extend in a first plane. Second, the open loop includes a first open loop extending or curling in a first path and a second open loop extending or curling in a second path, the second path being opposite from the first path. Third, the open loop may extend in a curl perpendicular to the filter leg and the sharp point may face the second end. In other words, the open loop may extend in a second plane being substantially perpendicular to the first plane of its respective filter leg. In any embodiment, the anchor may have a foot, the foot extending outward from the second end to control penetration of the wall.

The expandable introducer includes a slider connected to a plurality of introducer levers, each introducer lever extending to one of a plurality of filter carriers, each filter carrier terminating in the casing. In one embodiment, the anchor is a plurality of anchors and the casing is a plurality of casings.

In one embodiment of the filter unit, the filter unit includes a first filter unit having a first filter point (e.g. first center) and a second filter unit having a second filter point, the first and second filter points connected by a strut extending along the longitudinal axis. In this embodiment, the first and second filter units are disposed along the longitudinal axis.

These features give one possible advantage of the filter unit exerting about zero or minimal force on the vessel wall (i.e. radial force). In this case, the filter unit does not disrupt the natural vessel mobility or function. Such a filter is desirable in a flexible vessel. Additionally, the filter unit may not fatigue because there are about zero or minimal internal forces that may deform the filter unit over time. The internal forces of the filter can cause the filter to collapse or fatigue over time. As such, the filter may be less susceptible to wear.

Finally, because the anchors move between the straight state and the curled state, they may be removed from the vessel wall even after endothelialization has occurred. In the straight state, the anchors may slide out of new tissue growth, causing minimal trauma to the vessel wall.

BRIEF DESCRIPTION OF THE DRAWINGS

FIGS. 2A-C depict steps of one example of a method of filtering in a body vessel with an apparatus in accordance with one embodiment of the present invention;

DETAILED DESCRIPTION

The present disclosure provides generally for examples of a method of filtering in a body vessel (i.e. vena cava), which uses a flexible filter unit. The present disclosure also provides for examples of a low radial force filter apparatus. The accompanying figures are provided for general understanding of the structure of various embodiments. However, this disclosure may be embodied in many different forms. These figures should not be construed as limiting and they are not necessarily to scale.

All publications, patent applications, patents, and other references mentioned herein are incorporated by reference in their entirety. Unless otherwise defined, all technical and scientific terms used herein have the same meaning as those commonly understood by one of ordinary skill in the art to which this disclosure pertains. In the case of conflict the present disclosure and definitions will control.

"About" or "substantially" mean that a given quantity is within 10%, preferably within 5%, more preferably within 1% of the stated value.

"Adjacent" referred to herein means nearby, near to, or in close proximity with.

"Minimal" force or a derivative thereof referred to herein is about zero.

The terms "proximal," "distal," and derivatives thereof will be understood in the frame of reference of a physician using the apparatus. Thus, "proximal" refers to locations closer to the physician and "distal" refers to locations farther away from the physician (i.e. deeper in the patient's vasculature).

To "stitch" referred to herein is where an anchor attaches itself to the vessel wall by moving from a straight state to a curled state.

Figure 1A:
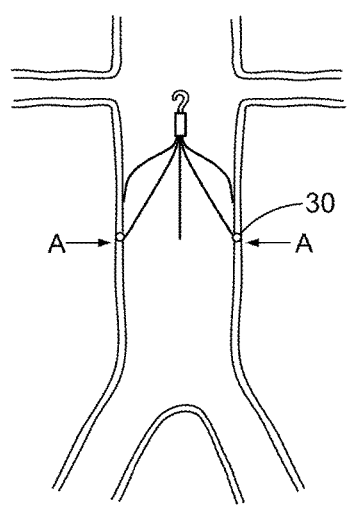
FIGS. 1A-C are environmental side and cross-sectional views of prior art.
Figure 1B:
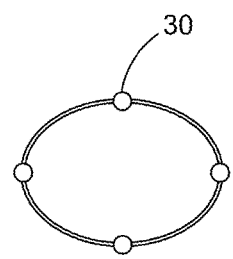
Figure 1C:
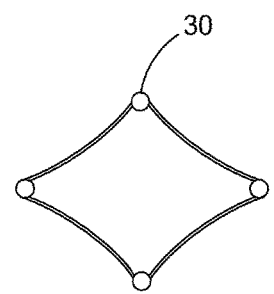

FIGS. 1A-C illustrate prior devices. FIG. 1A shows an implantable filter having contact points 30 against the vessel wall. Arrows A show a cross-section of the vessel. In FIG. 1B, cross-section A is shown, following implantation. Here, the vessel cross-section or shape is native (i.e. a circular configuration). However depicted in FIG. 1C, over time the contact points 30 may revert to the shape of the filter device, tenting the wall into a tent-like or rectangular shape.

FIGS. 2A-C depict steps of one method of filtering in a body vessel with a filter apparatus 10. The body vessel has a wall 40 and a longitudinal axis B. The body vessel is accessible from a femoral or jugular access point. The apparatus 10 includes the filter unit 50 and the expandable introducer 206. The filter unit has a filter point 42, which is generally in the center of the unit, and a plurality of filter legs 48, which extend from the filter point 42 in the filter unit 50. Filter legs 48 have a first end 44 at the filter point 42 that extends outward to a second end 46 away from the filter point 42. The second end 46 includes an anchor 52 being biased to curl.

The expandable introducer 206 may have a slider 64, which moves the apparatus 10 from its collapsed state 100 to its expanded state 102. The collapsed state may have an outer sheath (not shown) disposed about the apparatus for ease of delivery. In this embodiment, the slider 64 is connected to introducer levers 66. Introducer levers 66 extend to filter carriers 68. Together the slider 64, introducer levers 66, and filter carriers 68 create an umbrella-like configuration that supports the filter unit 50 during delivery. The expandable introducer 206 also has a casing 62 removably attached to the filter unit 50 at the anchor 52. The apparatus 10 has a collapsed state 100 and an expanded state 102 for attaching the filter unit 50 to the wall 40.

Figure 3A:
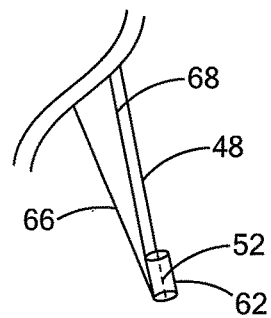
FIGS. 3A-D are partial side views of the apparatus of FIG. 2.
Figure 3B:
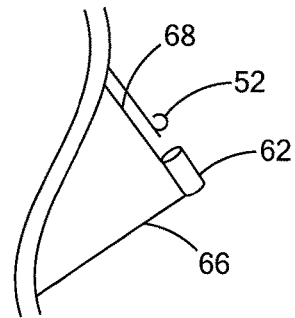

First in one example of the method, the physician positions the filter apparatus 10 in the body vessel. The filter apparatus 10 may have the anchor 52 disposed in the casing 62. Each filter carrier 68 of the expandable introducer terminates in the casing 62. The dashed circles in FIGS. 2A-B depict the casing location. Further details of the casing structure in FIGS. 2A-B are shown in FIGS. 3A-B. In the collapsed state for delivery, the casing 62 may surround or encase the anchor 52. This may keep the anchor 52 in a straight state upon delivery to the vessel wall.

Second in one example of the method, the physician may press or contact the anchor 52 against the wall 40 with the expandable introducer 206 by moving the apparatus 10 from the collapsed state 100 to the expanded state 102. After the step of positioning, the physician expands the expandable introducer, including moving the slider 64 to extend the filter carriers and introducer levers toward the wall 40. In other words, the expandable introducer 206 may position and push the anchors 52 at the filtering site. When the physician decides that the filter unit 50 is at the desired location, the physician may extend slider 64 to the expanded state 102. This expanded state 102 may push or press the anchors 52 against the wall 40.

Third in one example of the method, the anchor 52 is attached to the wall by removing it from the casing 62. During this implantation process, the anchors 52 may slide out of casing 62 and curl into or through the wall 40 to fix or attach to the wall. This attachment or fixing may hold the filter unit 50 in place. Once the filter unit is in place and attached to the wall 40, the expandable introducer 206 may be moved to its inverted state 104 using slider 64. This movement detaches the filter unit 50 and the expandable introducer 206. The anchors 52 may be substantially perpendicularly positioned in the wall 40, perpendicular to the longitudinal axis B and wall 40. In this condition, the open loop may extend in a second plane being substantially perpendicular to the first plane of its respective filter leg.

Alternatively, the anchors 52 may be substantially parallelly positioned in the wall 40 to the longitudinal axis B. In other words, each filter leg and its respective open loop may extend in a first plane. When attached or fixed as in FIG. 2C, the filter unit 50 may exert about zero or minimal radial force on the vessel wall through the filter legs 48. The filter unit 50 may be held in place solely by the anchors 52, each anchor 52 exhibiting the characteristics described herein. For example, the step of removing has the filter legs exerting about zero radial force on the wall 40. After the step of attaching the anchor 52, the physician may invert and withdrawn the expandable introducer 206 from the body vessel.

Figure 3C:
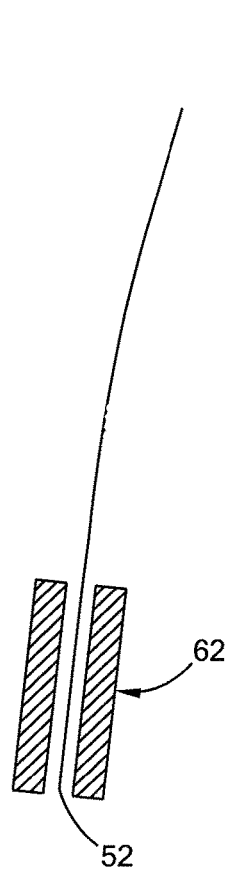
Figure 3D:
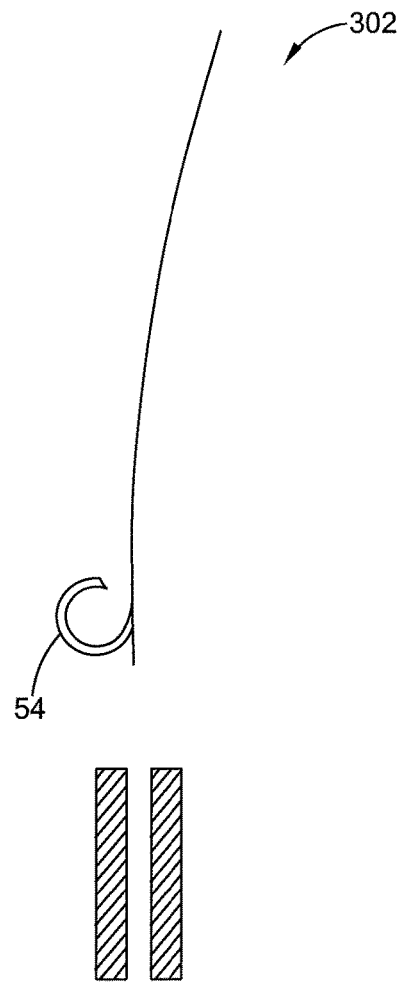

FIGS. 3A-D illustrate embodiments of an anchor in the straight and curled states, demonstrating how the step of attaching may have the anchor 52 curling from a straight state in the casing 62 to a curled state fixed to the wall 40. In addition at retrieval, the step of retrieving may have the anchor uncurling from a curled state fixed to the wall to a straight state for retrieval of the filter unit 50. FIG. 3A depicts a close-up view of anchor 52 disposed in casing 62 in the collapsed state. In this view, casing 62 may form a tight fit around anchor 52. In FIG. 3B, the apparatus expands, slidably removing anchor 52 from casing 62. Upon exiting casing 62, the anchor may curl into the open loop and stitch to the wall. In FIG. 3C, the anchor 52 is in the straight state 300 disposed in the casing 62. As the physician moves the anchor out of the casing by expanding the expandable introducer, the anchor 52 is slidably removed from of the casing 62. In FIG. 3D, the anchor curls into open loop 54 in the curled state 302.

The filter unit 50 may be made of any material to perform filtering. In one embodiment, the material may be a flexible or shape memory material (i.e. Nitinol). Alternatively, the material could be a polymer. In this embodiment, the filter unit could be formed by injection molding. In any case, the filter unit (specifically the filter legs) may be thin and flexible, of a material with no or minimal internal forces so as to exert minimal or about zero radial force on the wall. In addition, the anchors may be made of a bio-absorbable material, which would degrade after a predetermined time in the body (i.e. bio-absorbable metal).

Figure 4A:
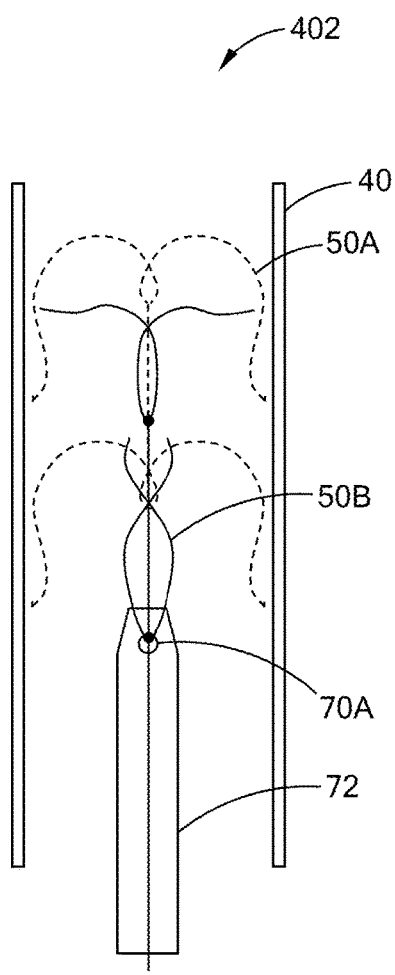
FIGS. 4A-B are side views of a filter unit of the apparatus of FIG. 2.
Figure 4B:
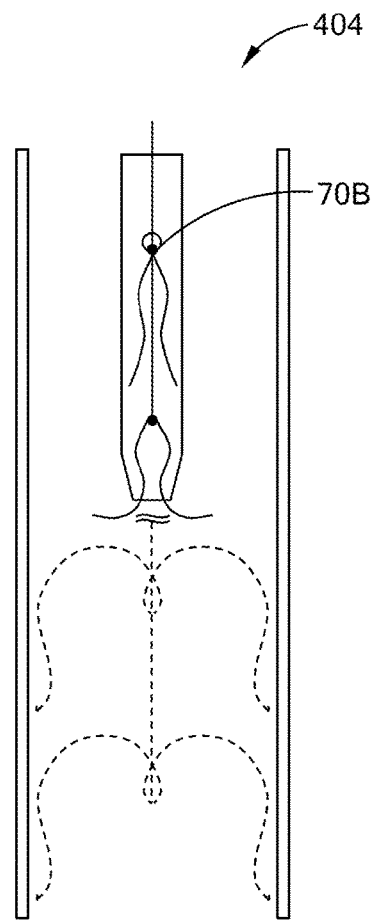

A retriever may be used to retrieve the filter unit after implantation through the femoral or the jugular access point. FIGS. 4A-B illustrate the retriever 72. FIG. 4A shows a femoral retrieval 402 and FIG. 4B shows a jugular retrieval 404. The filter unit may be retrieved using the Seldinger technique. In FIG. 4A, the filter unit 50 is implanted in position 50A. As shown, the retriever attaches or grabs the filter unit at retrieval point 70A. During retrieval the filter unit collapses from position 50A into position 50B due to the retriever. Alternatively in FIG. 4B, the retriever attaches at retrieval point 70B. It will be understood by one skilled in the art that the retrieval point could be anywhere on the filter unit because the filter unit may have minimal internal or radial forces. Therefore, any point that the physician can attach with the retriever may be sufficient to collapse and withdraw the filter unit into the retriever.

During retrieval, the retriever 72 slides the anchors 52 out of the vessel wall 40, uncurling them from the curled state to the straight state for retrieval of the filter unit. It is understood that the physician may apply (by way of the retriever) more force than the force of the anchor in the wall 40 to retrieve the filter unit. The anchors exit the wall in the straight state. In this state, the anchors can slide out of any endothelialization or tissue growth with minimal trauma to the wall, facilitating retrieval.

Figure 5A:
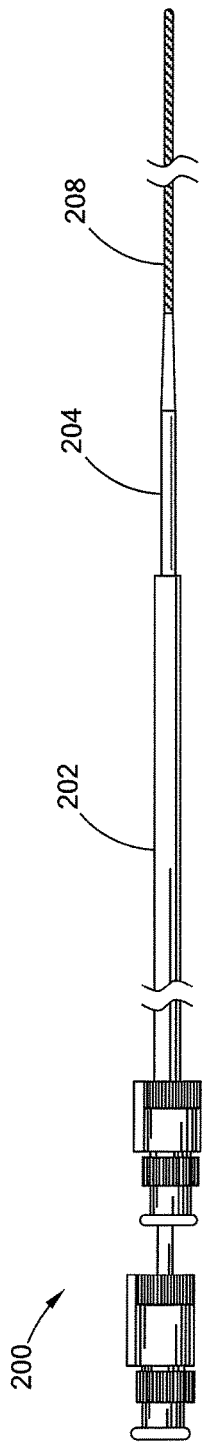
FIGS. 5A-B show a delivery assembly for introducing the apparatus of FIG. 2.
Figure 5B:
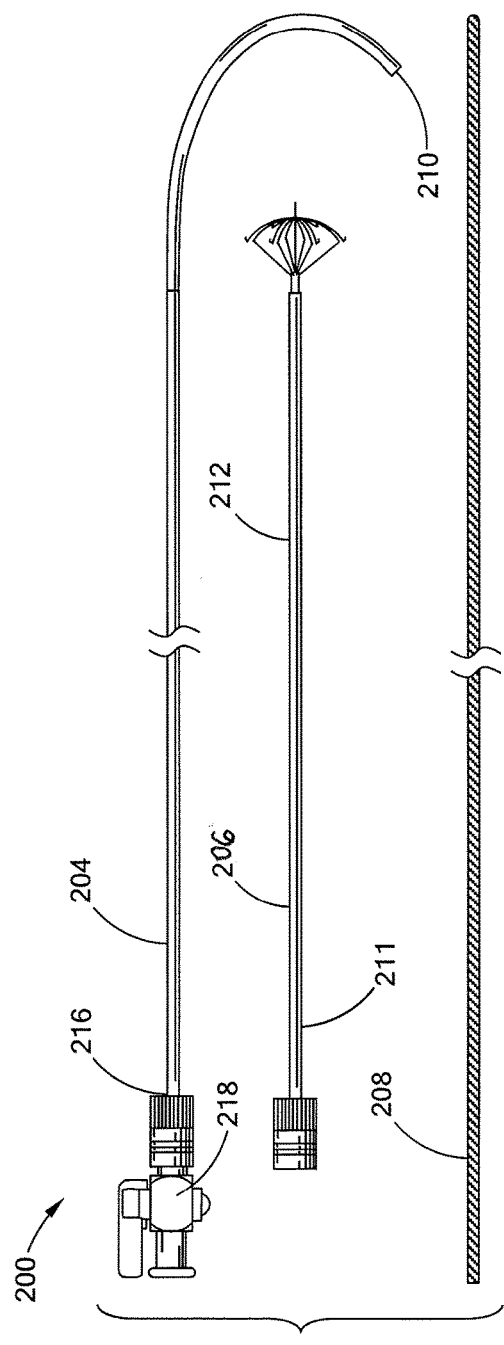

FIGS. 5A-5B illustrate a delivery assembly for introducing the apparatus according to the principles of the present disclosure. As shown, the delivery assembly 200 includes a polytetrafluoroethylene ("PTFE") introducer sheath 202 for percutaneously introducing an outer sheath 204 into a body vessel. Of course, any other suitable material for the introducer sheath 202 may be used without falling beyond the scope or spirit of the present invention. The introducer sheath 202 may have any suitable size; for example, between about 3-FR to 14-FR. The introducer sheath 202 may serve to allow the outer sheath 204 and the expandable introducer or catheter 206 to be percutaneously inserted to a desired location in the body vessel. The inner member may also include, for example, a stylet. The introducer sheath 202 receives the outer sheath 204 and provides stability to the outer sheath 204 at a desired location of the body vessel. For example, the introducer sheath 202 may be held stationary within a common visceral artery, and adds stability to the outer sheath 204, as the outer sheath 204 is advanced through the introducer sheath 202 to a filter area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the occlusion. The wire guide 208 provides the outer sheath 204 with a path to follow as it is advanced within the body vessel. The size of the wire guide 208 is based on the inside diameter of the outer sheath 204 and the diameter of the target body vessel.

When performing the Seldinger technique, a needle may also be used for percutaneously introducing the wire guide into the patient's body through an access site. A cutting device may also be used to expand the access site.

In one embodiment, when the distal end 210 of the outer sheath 204 is at the desired location in the body vessel, the wire guide 208 is removed and the filter unit, having a segment contacting a distal portion 212 of the expandable introducer 206, is inserted into the outer sheath 204. In FIG. 5B, the filter unit is shown expanded to depict the features of the device. It is understood that it may be delivered collapsed.

The expandable introducer 206 may be advanced through the outer sheath 204 for deployment of the filter unit through the distal end 210 to filter the body vessel. The expandable introducer 206 may extend from a proximal portion 211 to a distal portion 212 and is configured for axial movement relative to the outer sheath 204. In this example, the distal portion 212 is shown adjacent to the filter unit (as described herein). Thus, before deployment, the filter unit is coaxially disposed within the lumen of the outer sheath 204 and removably coupled or attached to the distal portion 212 of the expandable introducer 206.

The outer sheath 204 further has a proximal end 216 and a hub 218 to receive the apparatus advanced therethrough. The size of the outer sheath 204 is based on the size of the body vessel in which it percutaneously inserts, and the size of the apparatus. In this embodiment, the expandable introducer 206 is coaxially advanced through the outer sheath 204. In order to more easily deploy the filter unit into the body vessel, it may have a lubricious coating, such as silicone or a hydrophilic polymer, e.g. AQ® Hydrophilic Coating as known in the art. Likewise, the expandable introducer 206 may be withdrawn or retracted through the outer sheath 204.

It is understood that the assembly described above is merely one example of an assembly that may be used to deploy the apparatus in a body vessel. Of course, other apparatus, assemblies and systems may be used to deploy any embodiment of the apparatus without falling beyond the scope or spirit of the present invention.

Figure 6:
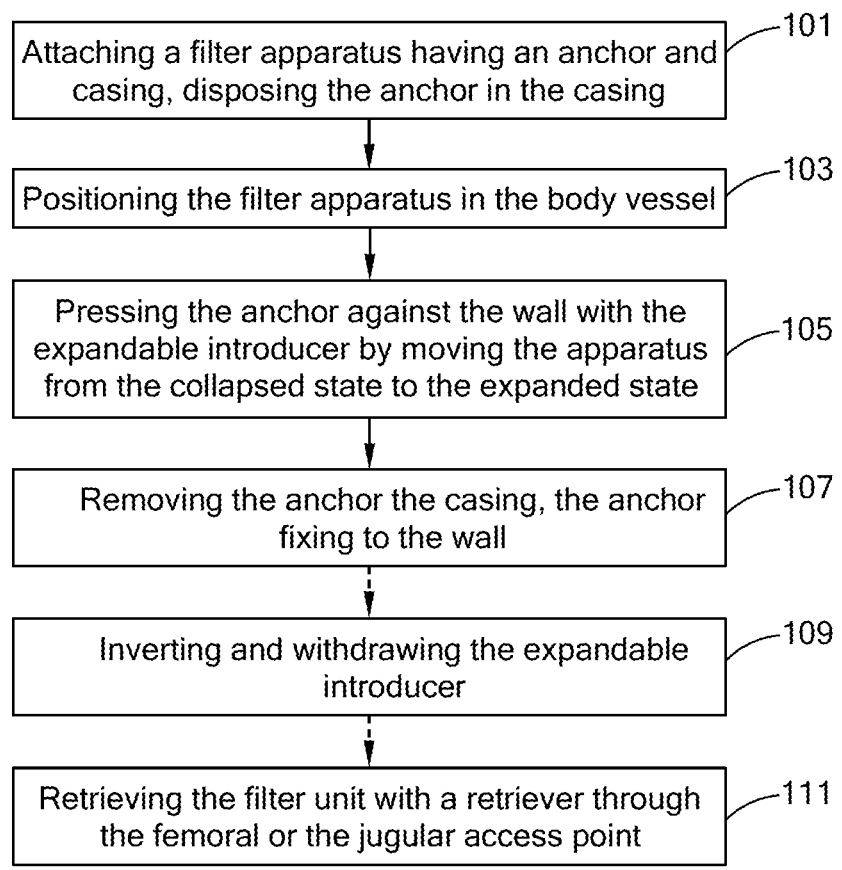
FIG. 6 is a flow diagram of the method of FIG. 2.

FIG. 6 illustrates steps of the method of filtering. In step 101, the physician may attach the filter apparatus having an anchor and a casing, disposing the anchor in the casing. In step 103, the physician may position the filter apparatus in the body vessel at the site intended for filtration. In step 105, the physician may contact or press the anchor against the wall with the expandable introducer by moving the apparatus from the collapsed state to the expanded state. In step 107, the user may attach the anchor to the vessel wall by removing it from the casing. In step 109, the physician may invert and withdraw the expandable introducer. In step 111, the physician may retrieve the filter unit with a retriever through an access point. It will be understood that the steps following removing the anchor shown in dotted arrows are optional steps. For example, the filter unit may have bioabsorbable anchors, which may require a different approach to retrieval.

Figure 7A:
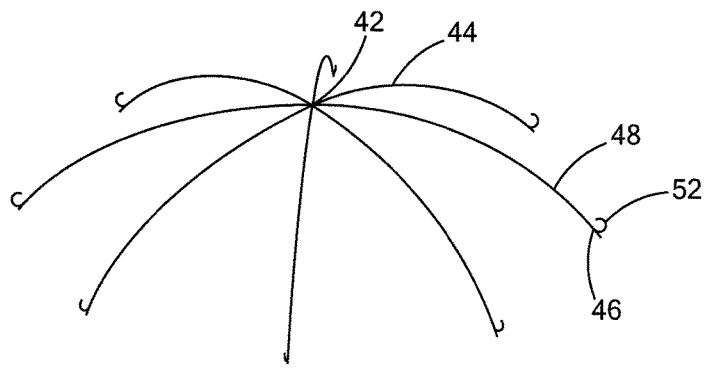
FIGS. 7A-E depict embodiments of a filter unit of the apparatus of FIG. 2
Figure 7B:
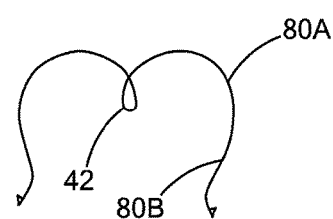

Embodiments for the filter unit 50 in the method will now be discussed. FIG. 7 depicts embodiment of the filter unit. FIG. 7A is a general depiction of the filter legs 48. The filter legs extend from the first end 44 at the filter point 42 to the second end 46. The second end terminates in anchor 52. Any suitable number of filter legs could be used. In one embodiment, the filter unit has eight to sixteen filter legs 48. The filter legs or pairs of filter legs may be joined by any method known in the art such as soldering, welding, tying knots, and interweaving.

Figure 7C:
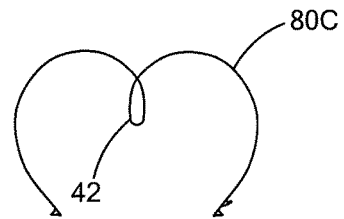
Figure 7D:
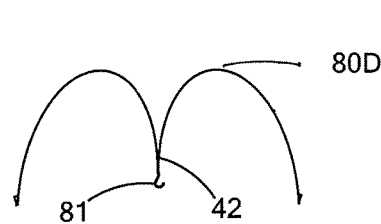
Figure 7E:
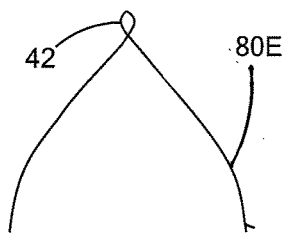

FIGS. 7B-E show exemplary shapes of pairs of filter legs. For example in FIG. 7B, the filter legs may form a loop at the filter point 42. In this embodiment, filter legs also have curves 80A and 80B at different points as the filter leg extends from the first end to the second end, each filter leg being spaced apart from an adjacent filter leg at the respective second ends. In FIG. 7C, the filter has curve 80C adjacent to the center. FIG. 7D shows curve 80D, about halfway between the first and second ends. In addition, the filter legs may have a hook 81 at filter point 42, which may be used for delivery or retrieval of the filter unit. In FIG. 7E, yet another possible embodiment, the filter unit has a loop at filter point 42 and a curve 80E adjacent to the second end.

The filter legs and their corresponding curves may have minimal internal forces to keep the filter point 42 close to the center of the body vessel. However, the filter point 42 may not line up with the center of the vessel. The anchors 52 may provide about equal distribution of the filter unit and prevent tilting against the wall.

Figure 8:
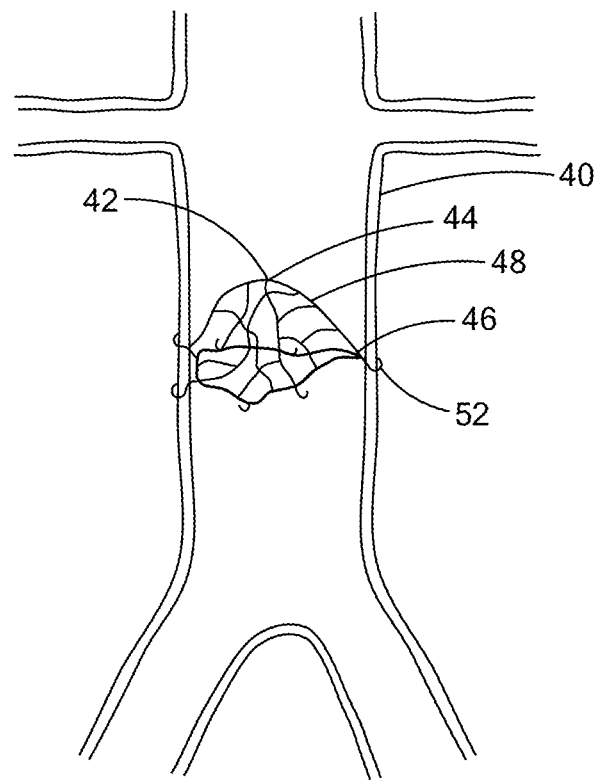
FIG. 8 depicts an embodiment of the filter unit of the apparatus of FIG. 2.

FIG. 8 shows another possible embodiment of the filter unit. In FIG. 8, the filter unit has filter legs 48 that formed into an interwoven net or mesh. This interwoven net also may exert minimal radial force against the wall 40.

Figure 9A:
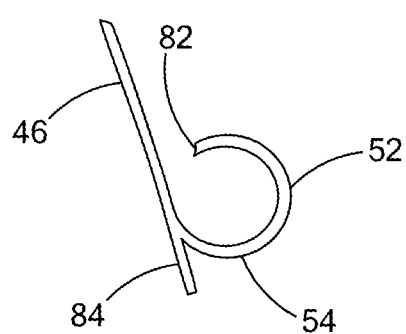
FIGS. 9A-B depict partial side views of the filter unit of the apparatus of FIG. 2.
Figure 9B:
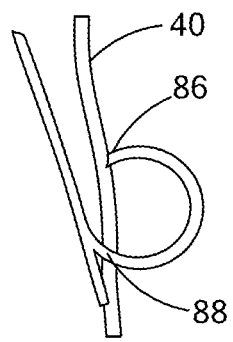

Embodiments of the anchor will now be discussed. FIGS. 9A-B illustrates an anchor. In FIG. 9A, the anchor 52 has a straight state for delivery and a curled state for fixing to the wall. In the curled state, the anchor 52 has an open loop 54 that may extend in a curl from the second end 46 to a sharp point 82. In this embodiment, the sharp point 82 is disposed to face one filter leg adjacent to the second end 46. In other words, the open loop 54 may extend completely in a plane that includes the longitudinal axis. The anchor also may have a foot 84, which extends from the second end 46. This foot may prevent further penetration into the wall 40 and provide a stop point. This foot 48 may also be radiopaque, such that it would have fluoroscopic properties. This allows the physician to view the location of the foot in vivo. FIG. 9B depicts a partial environmental side view. At point 88, the anchor has fixed or stitched itself, penetrating through the vessel wall 40. It has curled such that the sharp point 82 is embedded into wall 40 at an embedding point 86.

Figure 10A:
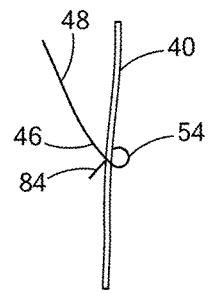
FIGS. 10A-C depict partial side views of the filter unit of the apparatus of FIG. 2.
Figure 10B:
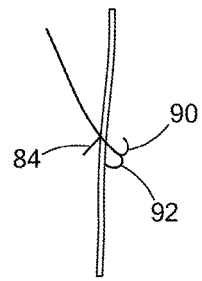
Figure 10C:
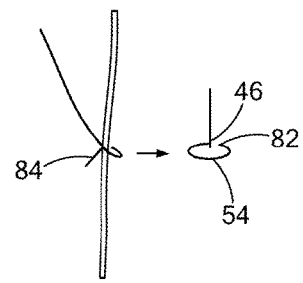

FIGS. 10A-C depict other possible anchor embodiments. In FIG. 10A, the foot 84 extends from the second end to prevent penetration. In FIG. 10B, the anchor depicted has a first open loop 90 and a second open loop 92. The first open loop extends in a first path and the second loop extends in a second direction such that the second direction is opposite from the first path. FIG. 10C shows yet another embodiment of the anchor 52 where the sharp point 82 penetrates wall 40 and extends or curls in a plane substantially perpendicular to a plane including the longitudinal axis. The open loop extends in a curl perpendicular to the second end 46 and curls around such that the sharp point 82 is disposed to face the second end 46. Such embodiments may have the embedding point.

While the anchors may penetrate the wall, it is understood that they may alternatively embed or stick into the inner side of the wall without penetrating through. Any of the anchors discussed herein may have the sharp point 82 embedded into the wall on the inner side without penetrating through the wall. In such an embodiment, it may be important to visualize the anchors to determine that they have not penetrated the wall with the radiopaque foot.

Figure 11:
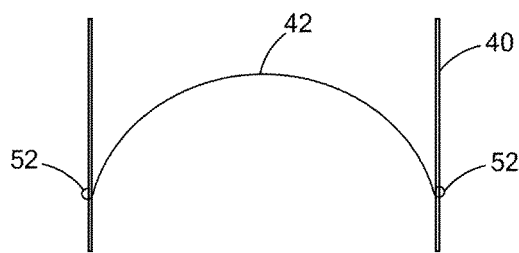
FIG. 11 is an environmental side view of the filter unit of the apparatus of FIG. 2.

FIG. 11 is an environmental view of a plurality of anchors. In this figure, a skilled artisan will appreciate that a pair of filter legs may extend the diameter of the body vessel and penetrate through the vessel wall 40 with two anchors 52. Although only a pair of filter legs are depicted here, more filter legs with respective anchors could be present, each having the features discussed herein. Correspondingly in this embodiment, the casing may be a plurality of casings, one for each anchor. In this figure, the foot is not shown. This full span of the diameter allows the anchors to provide equal distribution for the two filter legs from which the anchors are attached. It is understood that a similar configuration may be possible for all pairs of filter legs in the filter unit 50.

Figure 12:
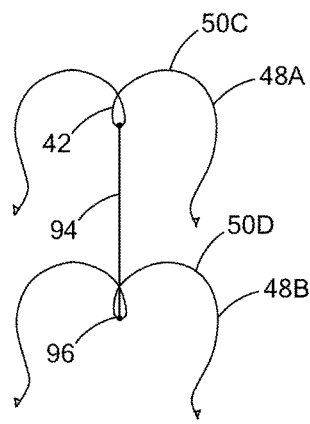
FIG. 12 depicts one example of the filter unit of the apparatus of FIG. 2.

FIG. 12 depicts yet another embodiment of the filter unit. In this embodiment, the filter unit is a pair of filter units including a first filter unit 50C with filter legs 48A and a second filter unit 50D with filter legs 48B. The first filter unit 50C has a first filter point 42 and the second filter unit 50D has second filter point 96. The two filter units are connected together via a strut 94, which may extend from the first filter point 42 to the second filter point 96. This pair of filter units connected by strut 94 may provide greater filtering capacity and stability for the filter unit within the body vessel. In this embodiment, the first and second filter units (50C and 50D, respectively) may be disposed along the longitudinal axis. All of the previously described aspects of the filter unit could be incorporated into the filter units in FIG. 11 or 12.

While the present disclosure has been described in terms of certain exemplary embodiments, it will be understood that the invention is not limited to those disclosed embodiments as those having skill in the art to make various modifications without departing from the scope of the following claims.

The invention claimed is:

1. A method of treatment in a body vessel having a wall, the method comprising:
   positioning a filter apparatus having an anchor disposed in a casing in the body vessel, the filter apparatus comprising:
      a filter unit having a filter leg comprising a first end extending to a second end including the anchor being biased to curl; and
      an expandable introducer having the casing removably attached to the filter unit at the anchor, the expandable introducer having a slider connected to a plurality of introducer levers, wherein the apparatus has a collapsed state and an expanded state for attaching the filter unit to the wall;
   moving the slider to extend the plurality of introducer levers to the wall;
   contacting the anchor against the wall by way of the expandable introducer by moving the apparatus from the collapsed state to the expanded state; and
   attaching the anchor to the wall by removing the anchor from the casing.

2. The method of claim 1 further comprising inverting the expandable introducer after the step of attaching the anchor.

3. The method of claim 2 further comprising retrieving the filter unit with a retriever through an access point after the step of inverting.

4. The method of claim 3 wherein the step of retrieving the filter unit comprises the anchor uncurling from a curled state attached to the wall to a straight state for retrieval of the filter unit.

5. The method of claim 1 wherein the anchor comprises bio-absorbable material.

6. The method of claim 1 wherein the step of attaching the anchor comprises the filter leg exerting about zero radial force on the wall.

7. The method of claim 1 wherein the step of attaching the anchor comprises the anchor curling from a straight state in the casing to a curled state attached to the wall.

8. A method of treatment in a body vessel having a wall, the method comprising:
   positioning a filter apparatus having an anchor disposed in a casing in the body vessel, the filter apparatus comprising:
      a filter unit having a filter leg comprising a first end extending to a second end including the anchor being biased to curl; and
      an expandable introducer having the casing removably attached to the filter unit at the anchor, wherein the apparatus has a collapsed state and an expanded state for attaching the filter unit to the wall;
   expanding the expandable introducer, the expandable introducer having a slider connected to a plurality of introducer levers, each introducer lever extending to one of a plurality of filter carriers, the step of expanding comprising moving the slider to extend the filter carriers and introducer levers to the wall;
   contacting the anchor against the wall by way of the expandable introducer by moving the apparatus from the collapsed state to the expanded state; and
   attaching the anchor to the wall by removing the anchor from the casing.

9. A filter apparatus for use in a body vessel having a wall, the apparatus comprising:
   a filter unit having a filter point and a plurality of filter legs extending from the filter point, each filter leg comprising a first end extending from the filter point to a second end comprising an anchor being biased to curl; and
   an expandable introducer having a casing removably attached to the filter unit at the anchor, the expandable introducer having a slider connected to a plurality of introducer levers, each introducer lever extending to one of a plurality of filter carriers, the slider being movable to extend the filter carriers and the introducer levers to the wall, wherein the apparatus has a collapsed state and an expanded state for attaching the filter unit to the wall, wherein each of the plurality of filter carriers terminates in the casing.

10. The apparatus of claim 9 wherein the plurality of filter legs forms an interwoven net.

11. The apparatus of claim 9 wherein each filter leg has a curve and is spaced apart from an adjacent filter leg at the respective second ends.

12. The apparatus of claim 9 wherein the anchor has a straight state for delivery and a curled state for attaching to the wall, the anchor comprising an open loop extending from the second end to a sharp point in the curled state.

13. The apparatus of claim 12 wherein each filter leg and its respective open loop extend in a first plane.

14. The apparatus of claim 12 wherein the sharp point is disposed to face its respective filter leg adjacent to the second end.

15. The apparatus of claim 12 wherein the open loop comprises a first open loop extending along a first path and a second open loop extending along a second path, the second path being opposite from the first path about the second end.

16. The apparatus of claim 12 wherein the open loop extends in a second plane substantially perpendicular to a first plane of its respective filter leg.

17. The apparatus of claim 9 wherein the anchor comprises a foot, the foot extending from the second end to control penetration of the wall.

18. The apparatus of claim 9 wherein the each filter leg of the plurality of filter legs comprises one anchor being removably attached to one casing.

19. The apparatus of claim 9 wherein the filter unit comprises a first filter unit having a first filter point and a second filter unit having a second filter point, the first and second filter points connected by a strut.

20. The apparatus of claim 9, wherein the filter legs extend proximally from the filter point and the introducer levers extend distally from the slider.

* * * * *